United States Patent
Brusasco et al.

(10) Patent No.: US 8,338,783 B2
(45) Date of Patent: Dec. 25, 2012

(54) DOSIMETRY DEVICE FOR VERIFICATION OF A RADIATION THERAPY APPARATUS

(75) Inventors: Caterina Brusasco, Bossiere (BE); Flavio Marchetto, Borgaro Torinese (IT)

(73) Assignees: Ion Beam Applications S.A., Louvain-la-Neuve (BE); Instituto Nazionale di Fisica Nucleare (INFN), Frascati (Roma) (IT); Departimento di Fisica Sperimentale, Università Degli Studi, Turin (IT)

( * ) Notice: Subject to any disclaimer, the term of this patent is extended or adjusted under 35 U.S.C. 154(b) by 868 days.

(21) Appl. No.: 11/996,653

(22) PCT Filed: Jul. 27, 2006

(86) PCT No.: PCT/BE2006/000085
§ 371 (c)(1),
(2), (4) Date: Jul. 31, 2008

(87) PCT Pub. No.: WO2007/012147
PCT Pub. Date: Feb. 1, 2007

(65) Prior Publication Data
US 2009/0200476 A1     Aug. 13, 2009

(30) Foreign Application Priority Data
Jul. 27, 2005 (EP) .................................. 05447177
Sep. 19, 2005 (EP) .................................. 05447206

(51) Int. Cl.
*G01J 1/00* (2006.01)
*G21K 1/02* (2006.01)
*G21F 3/00* (2006.01)
(52) U.S. Cl. ................. 250/336.1; 250/505.1; 250/515.1

(58) Field of Classification Search ................. 250/336.1
See application file for complete search history.

(56) References Cited

U.S. PATENT DOCUMENTS
3,678,233 A * 7/1972 Faw et al. .................... 378/158
(Continued)

FOREIGN PATENT DOCUMENTS
DE        38 44 716 C2     2/2001
(Continued)

OTHER PUBLICATIONS
Bonin R et al: "A Pixel Chamber to Monitor the Beam Performances in Hadron Therapy", Nuclear Instruments & Methods in Physics, Research, Section-A: Accelerators, Spectrometers, Detectors and Associated Equipment, Elsevier, Amsterdam, NL, vol. 519, No. 3, Mar. 1, 2004, pp. 674-686, XP004492326.
(Continued)

*Primary Examiner* — David Porta
*Assistant Examiner* — Carolyn Igyarto
(74) *Attorney, Agent, or Firm* — Fitch, Even, Tabin & Flannery, LLP (57) ABSTRACT

The present invention relates to a dosimetry device for verification of quality of a radiation beam in standard and conformal radiation therapy, and for IMRT (Intensity Modulated Radiation Therapy) applications. The device includes an active area comprising individual radiation detectors. The active area comprises a limited number of lines of radiation detectors, and a number of extra radiation detectors dedicated to the energy measurement of electrons or photons. It also comprises a build-up plate with energy degraders. The energy degraders are located upstream from the extra radiation detectors in the path of the radiation beam.

4 Claims, 9 Drawing Sheets

U.S. PATENT DOCUMENTS

| | | | |
|---|---|---|---|
| 4,988,866 | A | 1/1991 | Westerlund |
| 6,125,335 | A | 9/2000 | Simon et al. |
| 6,891,178 | B2 * | 5/2005 | Xing .................. 250/505.1 |
| 2003/0201403 | A1 | 10/2003 | Svatos et al. |

FOREIGN PATENT DOCUMENTS

| | | |
|---|---|---|
| DE | 101 43 609 A1 | 3/2003 |
| EP | 1 308 185 A2 | 5/2003 |
| WO | 94/28974 A2 | 12/1994 |

OTHER PUBLICATIONS

Brusasco C et al., "A Dosimetry System for Fast Measurement of 3D Depth-Dose Profiles in Charged-Particle Tumor Therapy With Scanning Techniques", Nuclear Instruments & Methods in Physics Research, Section-B: Beam Interactions With Materials and Atoms, Elsevier, Amsterdam, NL, vol. 168, No. 4, Aug. 2000, pp. 578-592, XP004206343, ISSN: 0168-583X.

Amerio S et al: "Dosimetric Characterization of a Large Area Pixel-Segmented Ionization Chamber", Medical Physics, American Institute of Physics. New York, US, vol. 31, No. 2, Feb. 2004, pp. 414-420, XP012074787, ISSN: 0094-2405.

Yang Yong et al: "Using the Volumetric Effect of a Finite-Sized Detector for Routine Quality Assurance of Multileaf Collimator Leaf Positioning", Medical Physics, AIP, Melville, NY, US, vol. 30, No. 3, Mar. 2003, pp. 433-441, XP012012014.

* cited by examiner

DOSIMETRY DEVICE FOR VERIFICATION OF A RADIATION THERAPY APPARATUS

FIELD OF THE INVENTION

The present invention is related to a dosimetry device and method allowing accelerator factory testing, commissioning, acceptance and quality assurance (QA) for verification of the quality of the radiation delivery in standard and conformal radiotherapy, as well as partial QA in IMRT (intensity modulated radio therapy) applications and tomotherapy applications.

STATE OF THE ART

In treating patients with radiation, the radiation oncologist prescribes a treatment regimen whose goal is to cure or control the disease by precisely delivering an optimal radiation dose to the tumor and reducing the side effects on healthy surrounding tissues. In general, published clinical and experimental results demonstrate that the response of tumours and normal tissues to radiation is highly variable. Moreover, for some tumours and normal tissues, the dose response curves may be very steep in the therapeutic dose range, i.e., a small change in dose can result in a large change in clinical response. In addition, the prescribed radiation dose to the tumour is usually, by necessity, constrained by the tolerance dose of the surrounding normal tissues. Consequently, since the "window" for optimal treatment can be quite narrow, the radiation dose must be delivered accurately and consistently.

Delivery of treatment in an accurate and consistent manner is by no means easy to achieve, since the radiation therapy process is a complex interweaving of a number of related tasks for designing and delivering radiation treatments.

Therefore, general prescriptions including particular dosimetry tests have been established in order to have a control and an (on-line) verification of said delivery of treatment.

Usually, these tests are performed at first at the release of a new radiotherapy device from production and then at its installation in a clinical institution in order to control that the expected dose is really delivered as required. These tests are performed by the accelerator manufacturers for the release from production and after any important maintenance intervention and by the medical physicist of the clinical institution for the device acceptance and commissioning in order to prove the compliance of the equipment to the norms set by regulation authorities.

Furthermore, regular tests based on a routine schedule have also to be performed by the users in order to check the behaviour of the radiotherapy device. Again, dosimetry tests are therefore performed. They are defined as quality assurance. Among others, recommendations for performing such tests for quality assurance are described in details in AAPM REPORT NO. 46 "Comprehensive QA for Radiation Oncology", published for the American Association of Physicists in Medicine by the American Institute of Physics, reprinted from MEDICAL PHYSICS, Volume 21, Issue 4, 1994.

A device able to measure field profiles, hereafter called beam profiler, is needed in order to perform some of the required dosimetry tests. Especially in an IMRT application, using a multi-leaf collimator (MLC), it is important to be able to determine the positions and penumbrae of the leaves of the MLC.

One of the most known instruments used in order to measure field profiles is the "water phantom" instrument. This dosimetry instrument is in the form of a water tank which uses a single detector that moves immersed in the water inside the tank, recording the dose profiles in the three dimensions. Although this device represents the golden standard in accelerator commissioning, acceptance and routine QA, thanks to its flexibility in recording the dose profiles, performing the needed measurements with it is a cumbersome and long lasting task: the water tank is a heavy and bulky device and takes long to set it up; the scans take time to be performed as normally only one detector is present, etc.

Other possible dosimetry equipments include devices comprising several radiation detectors performing such measurement, possibly in the form of matrixes or arrays. Two main families of such devices can be described: the one using diodes and the one using ionisation chambers.

An example of such devices using diodes is described in U.S. Pat. No. 6,125,335 wherein a beam profiler is in the form of an array of 46 sensor diodes, S1-S46 and 4 off-axis horizontal sensor diodes, S48-S51. An example of a typical beam profiler is the off-the-shelf multi-sensor radiation detector array entitled: Profiler Model 1170, manufactured by the assignee of the subject invention, Sun Nuclear Corporation of Melbourne, Fla. The Sun Nuclear Profiler generates a real time graphic image which is a trace of individual data points spaced approximately 5 mm apart and updated each second. The 46 diodes, S1-S46 and off-axis detectors S48-S51 provide a real time profile of the emitted radiation beams and off axis analysis. However, the main problem of these devices is the fact that they use diodes which have a non-linear response to dose, requiring accordingly complex calibration methods such as the one described in document U.S. Pat. No. 6,125,335.

Furthermore, compared to dosimetry equipments based on ionisation chambers, a device using diodes has a cost price per unit (pixel) higher than a device using ionisation chambers.

Another family consists in dosimetry instruments which implement arrays of ionisation chambers instead of diodes.

Recently, very efficient ionisation chamber arrays have been developed by Bonin et al. in "A pixel chamber to monitor the beam performances in hadron therapy" Nuclear Instruments and Methods in Physics Research A 519 (2004)-674-686. This document describes a device made up of a 2-D array of 1024 successive ionisation chambers arranged in a regular matrix of 32×32 pixels. The general principle of an ionisation chamber is as follows: a high voltage is applied between two electrodes. A gas (here air or nitrogen) present between the electrodes is ionised by the radiation traversing it. As a result of the electric field, the ions are collected on the electrodes, and the charge can be measured. As the creation of one electron-ion pair requires a known average energy, depending on the gas and on the irradiation type, the collected charge is directly proportional to the energy deposited in the gas. A recycling integrator circuit provides a 16-bit counter proportional to the detected charge. The recycling integrator was developed as a 0.8 µm CMOS technology chip (TERA06) by INFN (Istituto Nazionale di Fisica Nucleare, Torino). Each of these chips provides 64 channels. The minimum detectable charge is adjustable between 50 fC and 800 fC, and the read rate in the linear region can be as high as 5 MHz. As described above, the monitor comprises 32×32 air vented ionisation chamber pixels arranged in a matrix with a pitch of 7.5 mm.

Although this device is considered to be very efficient, its geometry, a matrix of 32×32 ionisation chamber pixels, is best adapted to the complexity of the dose distributions delivered in IMRT but well too complex and expensive for standard and conformal RT, where normally only the profiles on the main axis and diagonals are needed. Furthermore, the complexity of arranging such a high number of detectors and their read-outs in a matrix had an impact on the dimensions of such a device, which is not large enough to cover all the field dimensions which need to be checked both in routine QA and in accelerator commissioning/acceptance.

Another dosimetry device, using any type of radiation detectors, e.g. ionisation chambers or semiconductor detectors, is known from U.S. Pat. No. 4,988,866. This device comprises only a limited number of sensors, located at specific positions, for performing specific measurements. Therefore, it cannot verify the quality of a radiation field of any size, according to any recommended QA protocol. Moreover, with a single absorber, only a single radiation energy (or a very narrow energy range) can be measured.

Still another dosimetry device, using any type of radiation detectors, is known from DE-101 43 609. This device aims at improving the spatial resolution of measurement, without increasing the number of individual sensors (17). This result is obtained by installing a set of sensors (17, 17', and 17") on lines (19) on a support (7). The support (7) is rotatable around a bearing (18). The sensors on one line (17') are located at a different radius from sensors (17") located on another line. The support is successively rotated along an angle of 1° or 2°. From the successive measurements of e.g. 88 sensors on 100 angular steps, a set of 8 800 measurements points can be obtained, giving a much higher spatial resolution. However, this device requires a mechanical drive for the sensor, and the measurement is more time-consuming. In addition, because one takes a set of measurements at successive times, one relies on the stability and constancy of the radiation source. No means are provided for measuring radiation beam energy.

Although some of the devices of the state of the art are providing energy measurements e.g. by means of build-up plates of different thicknesses, they always need the user to enter several times into the treatment room to perform the measurement with the required build-up plate for different energies.

A method for determining the position of a leaf of a MLC has been described by Yang Y and Xing L in "Using the volumetric effect of a finite-sized detector for routine quality assurance of multi leaf collimator leaf positioning" Med. Phys. 30 433-441. According to this method, a finite-sized detector, such as an ion chamber, is located at the location of a leaf as projected in the isocenter plane. A leaf position error increase or decreases the irradiated volume of the detector. Therefore, a measurement of the dose can be related to the position error. However, no means are provided for measuring other parameters such as the radiation energy.

Accordingly, no practical solution is proposed to perform an easy and fast beam profile and energy measurement with a known device.

AIMS OF THE INVENTION

The present invention aims to provide a dosimetry device that does not present the drawbacks of the state of the art.

In particular, the present invention aims to provide a dosimetry device and a method which requires a limited number of individual radiation detectors while still providing the required accuracy, ease of use and fast operation.

Furthermore, the present invention aims to provide a device and a method which will not need the user to enter several times in the treatment room to perform the measurements.

A further aim of the present invention is to provide a device which also allows the fast and efficient measurement of the beam energy of electrons and photons.

The present invention also aims to provide a device which can be used for accelerator factory testing, commissioning, acceptance and quality assurance (QA).

A further aim of this invention is to provide a limited set of tests to be used in IMRT QA.

Finally, the present invention aims to provide a device having a reasonable price.

SUMMARY OF THE INVENTION

According with a first aspect, the present invention relates to a dosimetry device for verification of the quality of a radiation beam in standard and conformal radiation therapy, and in particular for IMRT (Intensity Modulated Radiation Therapy) applications, comprising an active area including a limited number of lines of individual radiation detectors dedicated to the measurement of the beam profile. Said active area further comprises extra radiation detectors dedicated to the energy measurement of electrons or photons, and a build-up plate, with energy degraders. Said energy degraders are located upstream said extra radiation detectors in the path of the radiation beam. Preferably, said extra radiation detectors are not located on the above-mentioned lines.

By limited number of lines, it should be understood at least two lines.

By line, it should be understood a linear arrangement of individual pixel.

In an advantageous embodiment of the invention, according to the first aspect, said radiation detectors are ionisation chambers.

In another advantageous embodiment of the invention, according to the first aspect, said radiation detectors are diodes.

In a typical embodiment of the invention, according with the first aspect, the limited number of lines is one set of two lines radiation detectors, said two lines being essentially orthogonal to each other.

Advantageously, this limited number of lines is one set of four lines of radiation detectors, said four lines being essentially oriented at an angle of 45° to each other.

In a specific embodiment of the invention, according with the first aspect, said energy degraders are either in the form of bumps of different thicknesses in said build-up plate and/or in the form of bumps or recesses with inserts of a different radiation absorbing materials.

Advantageously, said energy degraders are positioned in the quadrants or octants defined by said sets of lines dividing the active area, in the vicinity of the intersection of said lines.

In a specific embodiment of the invention, according with the first aspect, the invention is adapted for determining positions of leaves of a MLC in an IMRT radiation therapy apparatus. In this embodiment said limited number of lines of radiation detectors comprises further extra line(s) of radiation detectors dedicated to the measurement and determination of the projection of said leaves position at the isocenter of said IMRT radiation therapy apparatus, said one or more extra lines of radiation detectors being located at or near the positions where the leaves are expected to project.

Advantageously, according with the first aspect, said extra lines of radiation detectors comprises at least three parallel extra lines of radiation detectors on two opposite sides of said dosimetry device.

A second aspect of the invention relates to a method for verifying quantities of interest of a radiation beam in radiation therapy apparatus comprising an MLC provided with leaves, or jaws. This method comprises the steps of: providing a dosimetry device comprising one or more line of radiation detectors; positioning the leaves of the MLC or the single jaw in a predetermined position; delivering a radiation dose to said dosimetry device through said MLC or through said single jaw; measuring the dose absorbed by a plurality of radiation detectors of a line of radiation detectors located in the penumbra region of said leaf; determining all the quantities of interest in the penumbra region created by said leaf by fitting said measured doses with a function which recalls the shape of the field penumbra. Said quantities of interest may comprise the position of one of said leaves or jaws, the position and/or width of penumbra region, the positions where a beam profile reaches a given percent (e.g. 20% and 80%) of the value of the beam in the centre of the beam, the skewness of the beam, the flatness of the beam and the position of the centre of the radiation beam. By using this method, one can improve the spatial resolution of the measured profiles in the penumbra region and therefore precisely determine quantities of interest like the positions where the profile reaches a given percent of the value in the field central axis.

In a preferred embodiment of the method according to the second aspect of the invention, said function is a Fermi function and one determines the position of said leaf as the position corresponding to the 50% value of said Fermi function.

Advantageously, according to the second aspect of the invention, one determines the penumbra p according to the expression p=B/a, where B is a parameter selected between 2 and 3. If one defines the penumbra as the region where the dose goes from 80% to 20%, the correct value of B is 2.77

In another preferred embodiment of the method according to the second aspect of the invention, said step of providing a dosimetry device comprising three or more lines of radiation detectors, said lines being parallel to each other, and perpendicular to the leaf travel direction, radiation detectors on said lines being located under the projection of leaves of said MLC, thereby allowing the simultaneous determination of the positions and/or penumbrae of a plurality of leaves.

In accordance with a third aspect of the invention, there is provided a use of the device of the invention for performing method according to the invention.

DETAILED DESCRIPTION OF PREFERRED EMBODIMENTS OF THE PRESENT INVENTION

In relation to the appended drawings, the present invention is described in details for an embodiment using ionisation chamber technology.

It is apparent however that a person skilled in the art can imagine several other equivalent embodiments or other ways of executing the present invention, such as suggesting diodes instead of ionisation chambers for the radiation detectors, the spirit and the scope of the present invention being limited only by the terms of the claims.

Figure 1:
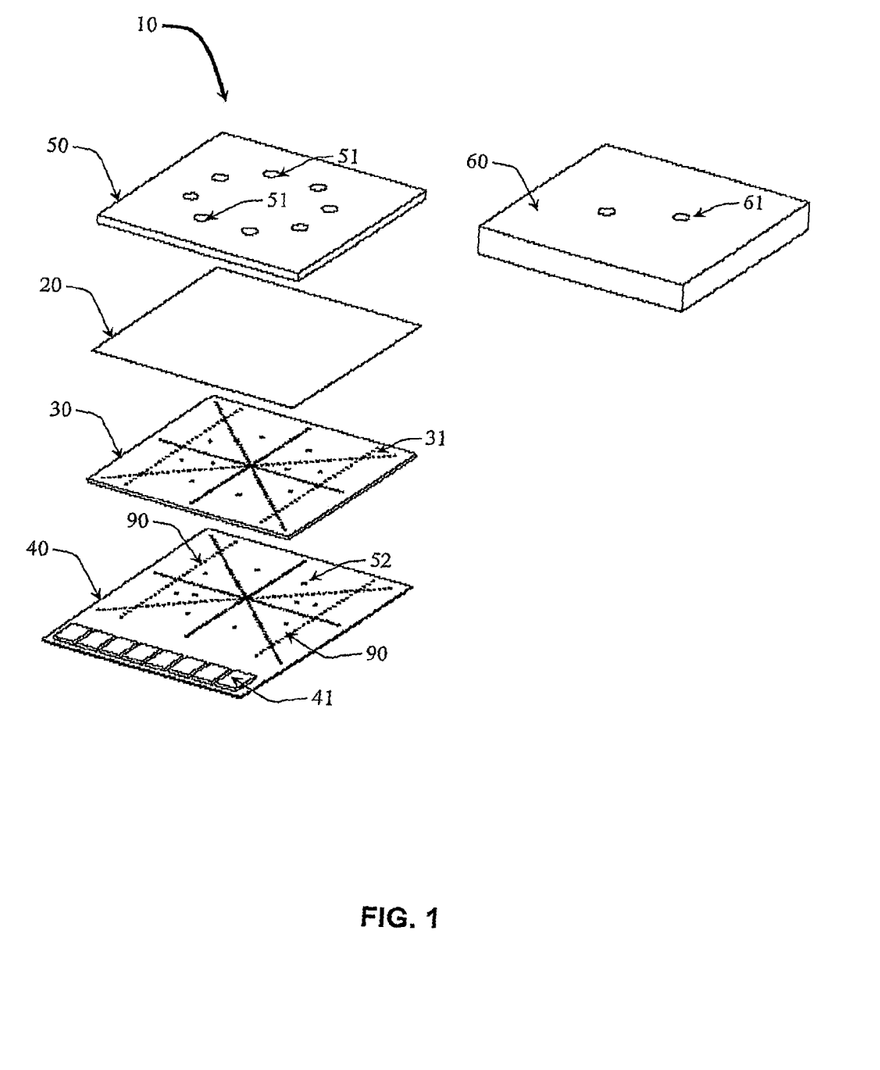
FIG. 1 and FIG. 3 represent, respectively, an exploded view of a device and a top view of the bottom-layer of said device according to one preferred embodiment of the present invention.

FIG. 1 represents an exploded view of a device according to a preferred embodiment of the present invention, which is using ionisation chambers in order to perform dosimetry tests. This dosimetry device 10 essentially consists in a stack of three main planar components:
1) a top layer 20, constituting the electrode top layer;
2) a mid layer 30 wherein drilled holes 31 delimit the gas volumes of the ionisation chambers;
3) a bottom layer 40 being the segmented electrode and carrying also the electronic chips 41 and the tracks bringing the signals from the ionisation chambers to the electronic chips 41;
4) either a removable build-up plate 50 for electron beams with energy degraders 51, or a removable build-up plate 60 for photon beams, with energy degraders 61.

Figure 2:
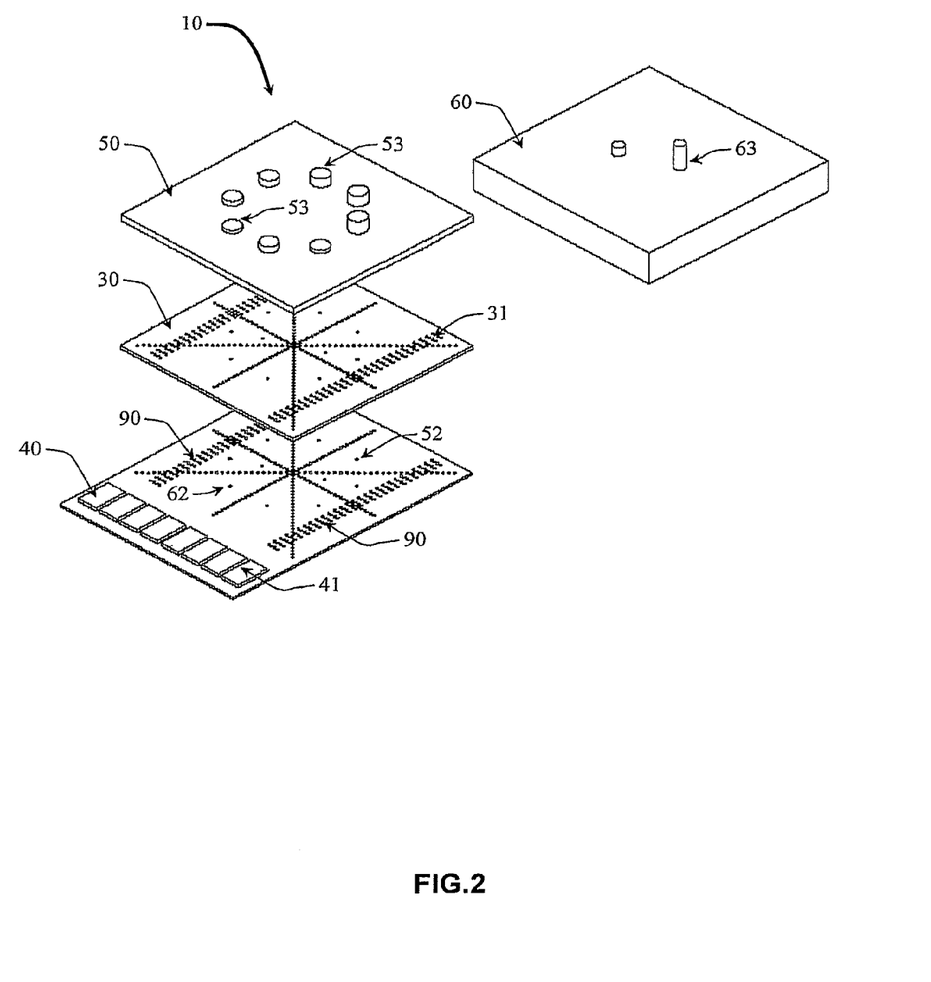
FIG. 2 and FIG. 4 represent, respectively, an exploded view of a device and a top view of the bottom-layer of said device according to another preferred embodiment of the present invention.

According to an important aspect of the present invention, as shown in FIG. 2, extra radiation detectors 52 are dedicated to the measurement of the energy of the electrons. Therefore, on the build-up plate 50 covering the top layer 20 of the dosimetry device 10, and dedicated to the electron beam measurements, a set of degraders 53 of different materials or different thicknesses having a different water-equivalent thickness from one degrader to the other are embedded in the build-up plate 50. Preferably, the combination of materials and thicknesses of said degraders gives an increasing water-equivalent thickness within a range comprised between 5 to 100 mm, while the build-up plate has a thickness which allows measuring the field profiles of all the electron energies (10 mm water-equivalent in the preferred embodiment of FIG. 1). Of course, said degraders 53 are placed on top of radiation detectors so that the electrons detected by such radiation detectors have been crossing the degraders before entering the active volumes of them.

The general principle of an ionisation chambers is again explained hereunder.

The radiation traversing the chambers ionises the gas present in between the top layer and the bottom layer. When a high voltage is applied between the two electrodes, an electric field is created and the ions are collected on the electrodes thereby creating a signal which can be measured.

The technology used for manufacturing these ionisation chambers can be any one described in the state of the art and can be for example the one described by BONIN et al. using the so-called TERA electronics.

Figure 3:
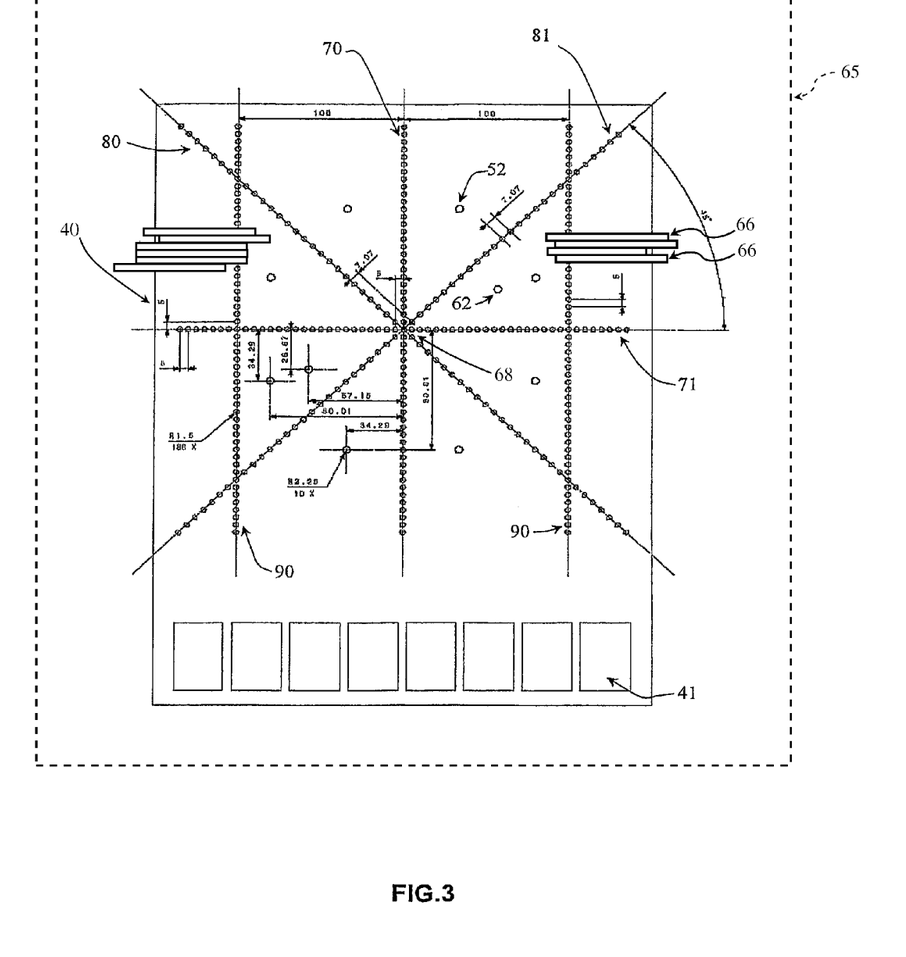

Further, FIG. 3 includes a schematic representation of a collimator 65, shown in dashed lines, having a plurality of collimator leaves 66 and an isocenter at reference number 68.

Figure 4:
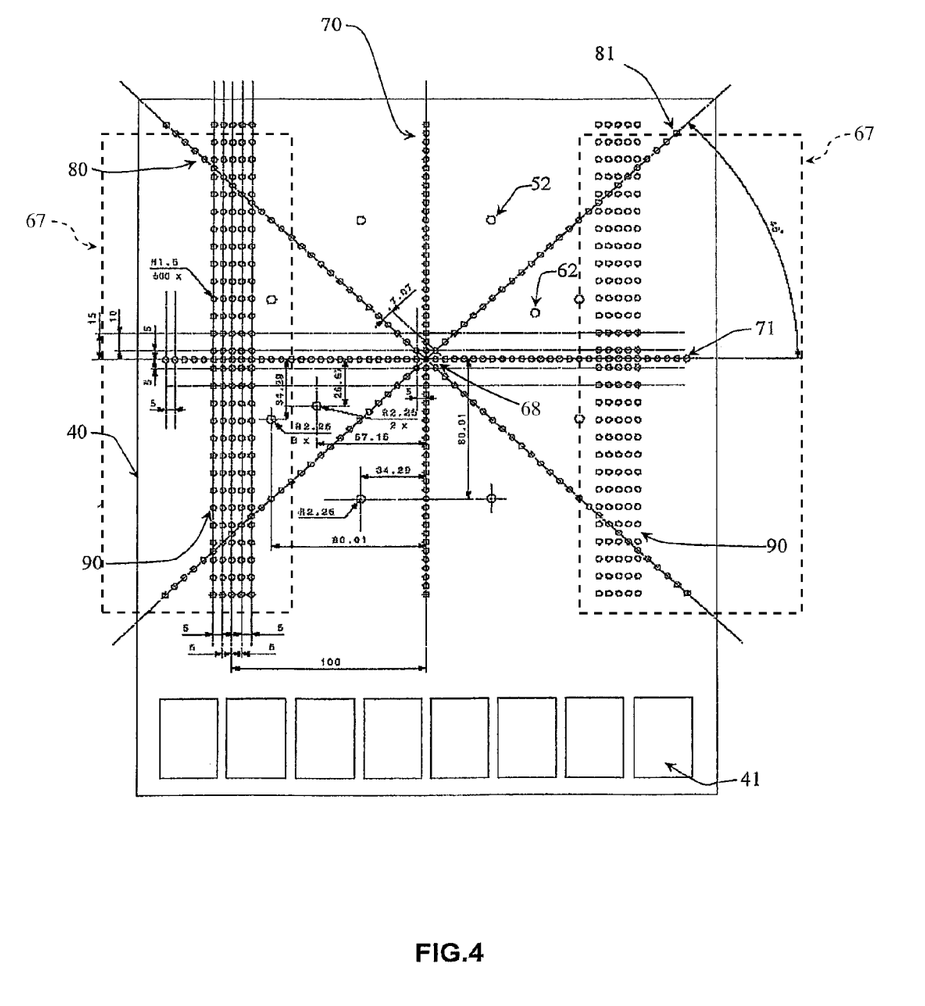

FIG. 4 includes a schematic representation of the collimator 65 having jaws 67 and an isocenter at reference number 68.

Figure 4B:
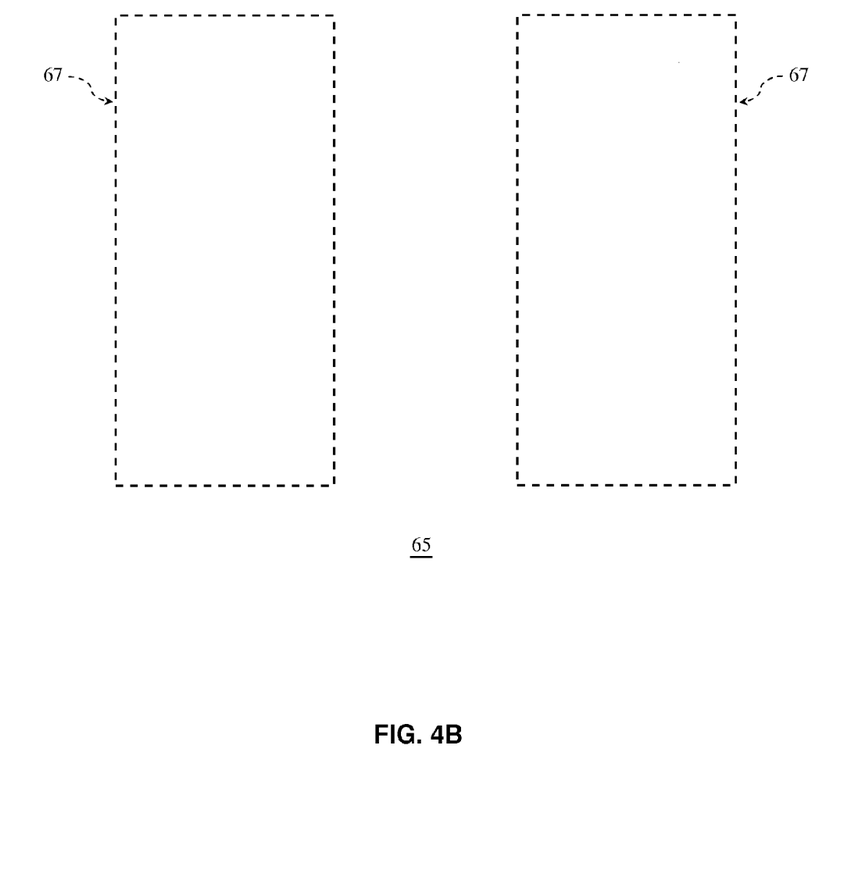
Figure 5:
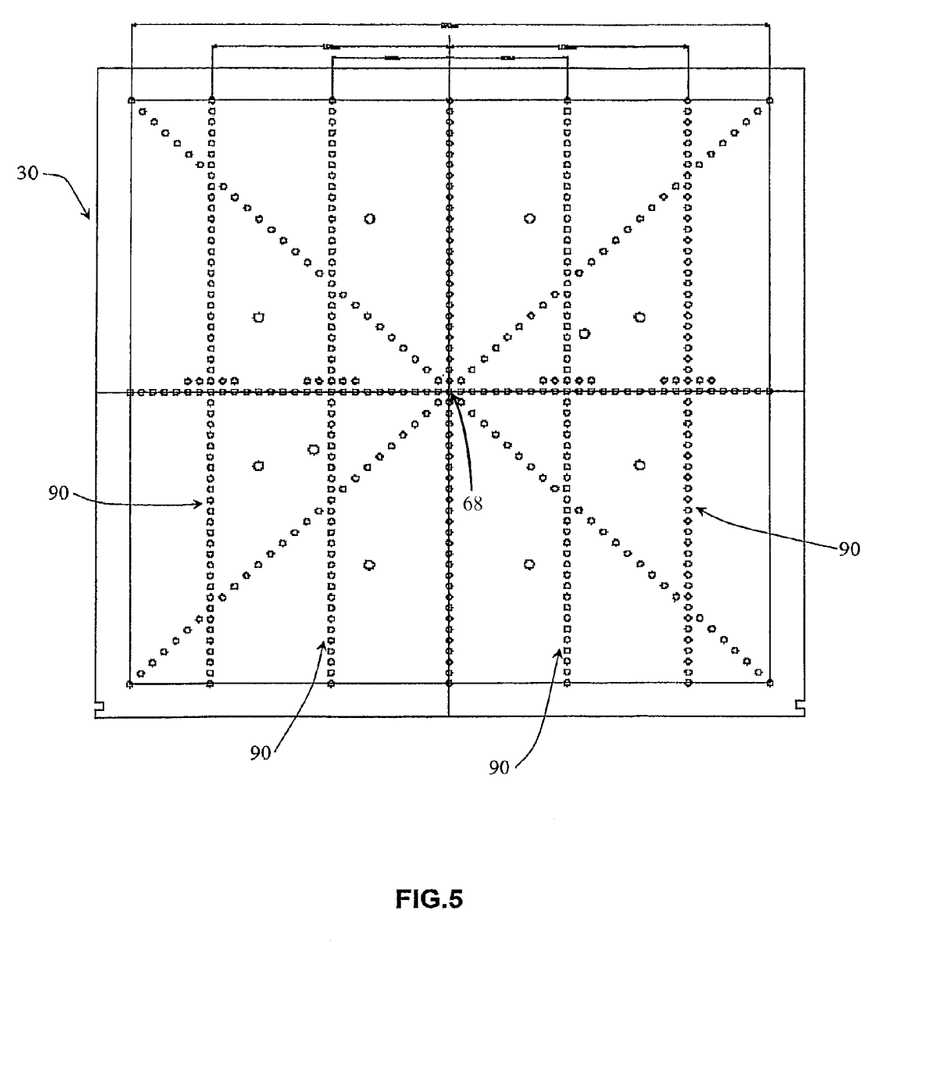
FIG. 5 represents a top view of the mid-layer of a device according to another preferred embodiment of the present invention.

FIG. 4B is a schematic representation of a collimator 65 having jaws 67, as shown in dashed lines.

According to a preferred embodiment, the dosimetry device can comprise, in particular, the following layers:

the top layer constituting the top electrode: a 50 µm thick printed Polyimide (Pyralux AP 8525R) layer covered with 25 µm carbon layers on both sides. The inner layer is structured according to the holes of the mid layer with a round shape of e.g. 0.1 mm smaller than the holes diameter (diam. 2.8 mm). The top carbon layer acts as an EMC shield;

the mid layer: a layer which consists in an approximately 5 mm thick pure polycarbonate plate with drilled holes of e.g. 3 mm diameter and spaced from each other over a length of 5 mm; ventilation can also be provided; therefore the mid layer is laminated to the top and to the segmented electrode on the bottom layer by means of adhesive dots that act as standoffs;

the bottom layer: a layer manufactured according to printed circuit board (PCB) techniques. An example of such a bottom layer using PCB techniques is described in the US provisional application filed in the name of the inventors of the present patent application on May 27, 2005, this document being incorporated by reference in the present application.

FIG. 3 represents a preferred configuration of an active area for one preferred embodiment of the present invention, wherein the active area is constituted by individual radiation detectors being ionisation chambers radiation detectors. However, exactly the same configuration can apply to diode radiation detectors.

According to the present invention, said configuration consists in at least one set of two essentially orthogonal lines of radiation detectors. Said lines are preferably passing through the centre of the active area and comprise preferably the majority of the radiation detectors present in said active area. In such case, one should assume that the two lines comprise m and n radiation detectors respectively, n and m being integers and higher than 1.

More preferably, said preferred configuration consists in at least two sets of essentially orthogonal lines of radiation detectors, said lines passing preferably through the centre of the active area and comprising preferably the majority of the radiation detectors present in said active area.

One can say that the configuration of the active area consists in a limited number of lines of radiation detectors. By "limited" number of lines, it should be understood at least 2 and strictly less than the number of radiation detectors of any line. In order to have a line, the number of radiation detectors should be an integer of at least 3 but preferably of at least 10, and more preferably of at least 20.

Furthermore, "limited" number of lines means equal to or less than 8, more preferably equal to or less than 4, more preferably equal to 2.

However, said configuration of radiation detectors does not cover all the surface of the mid layer. Said configuration cannot be considered as a matrix defined as an n×m radiation detectors matrix which corresponds to an embodiment of the state of the art, n and m being the number of radiation detectors of any two orthogonal lines.

Accordingly, the total number of radiation detectors of the present invention is a linear function f(n+m), or f(n) if n=m, while the number of radiation detectors for an embodiment of the state of the art (matrix configuration) is a function f(n×m), or $f(n^2)$ if n=m.

Another way to understand the present invention can be as follows: only very few radiation detectors are present in the area divided by the lines, namely in the quarters, if the division of the active area is performed by one set of two lines, or in the octants, if the active area is divided by four lines.

If we compare the number of radiation detectors used in a device built according to the state of the art and in a device according to the present invention, it is obvious that the present invention implies a device with a lower number of radiation detectors and, accordingly, with a lower price. But if we build a device having a larger number of radiation detectors or even the same number of radiation detectors as, for instance, the device as described by Bonin et al., namely a dosimetry device having 32×32 radiation detectors (1024 radiation detectors), a device according to the preferred embodiment of the invention having two sets of two lines of 256 radiation detectors each will show either a surface for the active area (up to 8×, which is actually unrealistic) higher than the device suggested by Bonin et al. with comparable results relating to the measurements of the beam profiles or with a configuration with a (down to 8×, which is actually unrealistic) smaller pitch than the device suggested by Bonin et al. and then able to give a more precise result for the measurement.

Of course, in practice, a compromise of these several requirements is sought:

reduction of the total number of radiation detectors, while increasing the surface of the active area, while decreasing the pitch between two consecutive radiation detectors.

As represented on FIG. 3, the two rows (70 and 71) of the first set essentially consist in the median lines (longitudinal and transversal axes) of the active area, while the two rows (80 and 81) of the second set essentially consist in the diagonals of said active area, all of them passing through the centre O, the shape of the active area of said active area being essentially a square of e.g. between 200×200 mm² to 400×400 mm².

Preferably, each row or line (70, 71, 80 or 81) comprises at least 50 radiation detectors with a pitch less than 7 mm and preferably less than 5 mm and even preferably less than 4 mm.

According to a particular embodiment, the pitch on the median lines and the diagonal lines can be the same.

According to another preferred embodiment, the pitches are different on the median lines and on the diagonal lines. For instance, the pitch on the diagonal lines corresponds to $\sqrt{2}$ times the pitch on the median lines.

By "line", "row" or "column" of radiation detectors, one should understand either individual radiation detectors placed on a line or in staggered rows, within a certain width (as small as possible) along a line, said "line", "row" or "column" comprising at least 3 radiation detectors, preferably at least 10 radiation detectors and more preferably at least 20 radiation detectors.

Figure 6:
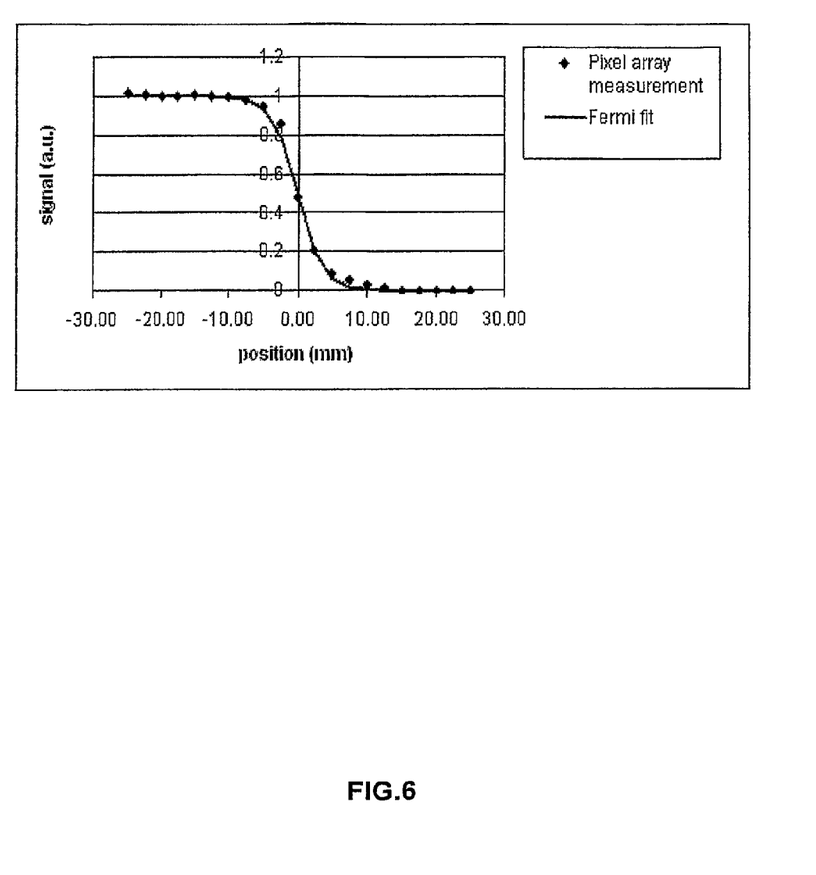
FIG. 6 shows an example of the penumbra of a field profile, as measured with one row of radiation detectors and as fitted with a Fermi function.

The spatial resolution of the measurements at the field penumbras and field gradients can be, according to a preferred embodiment, improved in respect to the spacing of the radiation detectors by applying a data interpolation based on the well known Fermi function:

$$F(x) = \frac{1}{1 + e^{a(x_0 - x)}}$$

wherein the dose in the homogeneous part of the field is normalized to 1, as shown in FIG. 6; $x_0$ represents the 50% position of the normalized dose; and the 20% to 80% distance (generally indicated as penumbra) is estimated by the relation a=2.4/p.

By applying such an interpolation, the precision in identifying the field penumbra, the field width and all the field related quantities determined in the penumbra region is improved to a fraction of 1 mm for a pitch of 5 mm.

The fact that the individual radiation detectors are placed in lines allows the acquisition of the field profiles in a one-step measurement, thereby avoiding any moving or manipulation of the dosimetry device. Said measurement can be considered as instantaneous. Thanks to its fast electronics, the device can also be used as a "real time" measurement device, allowing the steering of some accelerator parameters while observing the modifications induced on the measured profiles.

Furthermore, the fact that the radiation detectors organised in lines are not covering the whole surface of the active area will obviously reduce the price of the electronics attached to said dosimetry device and accordingly the final price of the dosimetry device.

According to another aspect of the present invention, in order to be able to cover field sizes bigger than the detector active area, the device can be coupled with a frame holding it at a source-axis distance (SAD) less than 100 cm.

Optionally, to provide a measurement dedicated to IMRT QA and more specifically to Multi Leaf (ML) Collimator QA as represented in FIGS. 1, 2, 4, 5, one or several lateral (vertical) bands 90 of radiation detectors are provided at different positions. Each band is composed of a few (typically 3 to 5) columns or rows of radiation detectors with a spacing of 0.5 or 1 cm corresponding to the leaf width if the plane of measurement is at isocenter in the longitudinal (i.e. vertical on FIGS. 1, 2, 4, 5, or perpendicular to leaf travel direction) direction, with a pitch of 2 to 8 mm in the transversal (i.e. horizontal on FIGS. 1, 2, 4, 5, or parallel to leaf travel direction) direction. When there are two bands centered at +/−10 cm, the detector is placed at isocenter and the several leaves are positioned as to give a 20×20 cm$^2$ field on the detector, each transversal row of a few radiation detectors is then providing the measurement of the position of a single leaf, again by using a Fermi fit on the measured penumbra, with a spatial precision of a fraction of 1 mm.

Another embodiment can provide only one row (FIGS. 1, 3, 5) of radiation detectors which are dedicated to the leaf measurement, in place of the bands of rows. In this case, a comparison of the relative signal of each radiation detector provides a relative position of the leaves. This design allows the verification of the position on the leaves of a MLC for a limited, predetermined set of leaf positions, where said leaf positions project on the isocenter plane.

According to the preferred embodiment described in FIG. 2, eight degraders 53 and corresponding radiation detectors 52 are placed on the periphery of a circle included in a 20×20 cm$^2$ field. Of course, the energy degraders 53 are placed not too close to the radiation detectors 52 present in the several rows intended to measure the field profiles, in order not to disturb the simultaneous acquisition of the field profiles.

According to another important feature of the present invention, extra radiation detectors 62 can be dedicated to the measurement of the energy of the photons. Therefore, on a build-up plate 60 covering the top layer 20 of the dosimetry device 10 and dedicated to the photon measurements, several extra energy degraders 63 are provided within a given field at isocenter (10×10 cm$^2$ in the preferred embodiment of FIG. 1). Said degraders have different water equivalent thicknesses within a range comprised between 5 to 200 mm (in the preferred embodiment of FIG. 1, two degraders corresponding to 10 and 20 cm water-equivalent respectively), while the build-up plate 60 has a thickness equal or higher to Dmax of the maximum photon energy measured (50 mm water-equivalent in the preferred embodiment of FIG. 1). Again, said degraders are placed on top of radiation detectors 62 so that the electrons detected by them have been crossing the degraders 63 before entering the active volumes of them.

The detectors dedicated to the measurement of energy may have different dimensions than the detectors present on the rows, (70, 71, 80 and 81).

Three possibilities are provided in order to realise the variation of the water-equivalent thickness of the degraders and accordingly the variation of the energy absorption:
- either having bumps on the build-up plate with different thicknesses,
- or having bumps on the build-up plate made of different materials and thicknesses or recesses with inserts in the thickness of the build-up plate, again made of different materials and thicknesses,
- or combinations of the above possibilities.

Once again, the fact that several energy degraders are present on each build-up plate will allow an energy measurement which can be performed in one step together with the relative field profiles, without any moving or any manipulation of said dosimetry device and build-up plates. Therefore, there is no need for an operator to enter the treatment room for changing a build-up plate.

Figure 7:
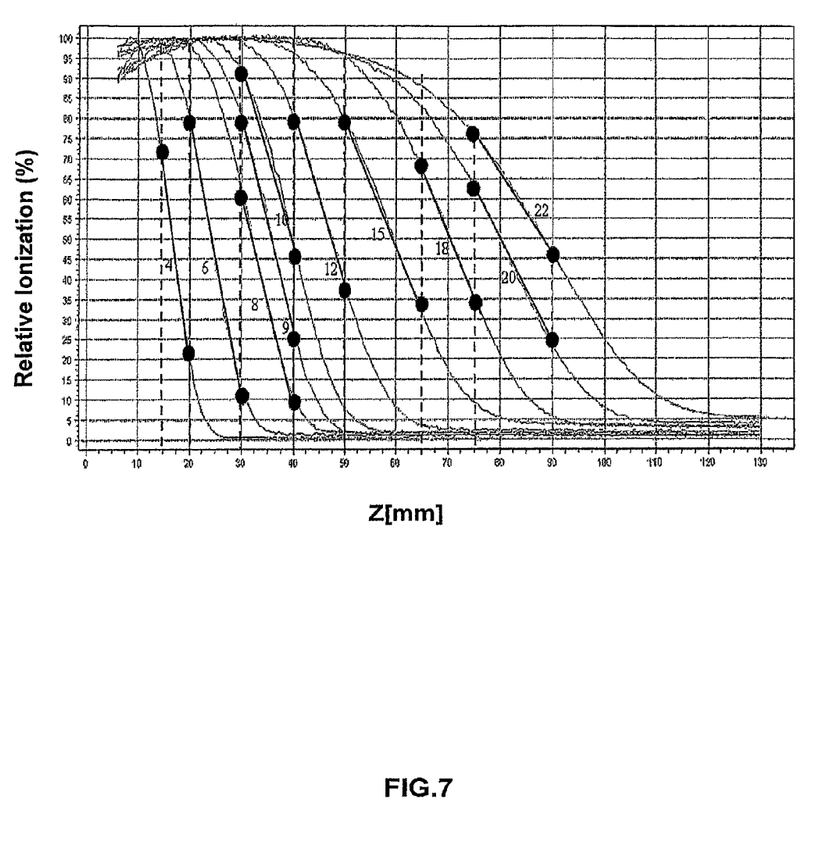
FIG. 7 shows the measurement points for electron energy measurement, from 4 to 22 MeV, obtained by eight ionisation chamber radiation detectors beneath the corresponding energy degraders present on the electron build-up plate of the device as described in FIG. 1.

The results of the energy measurement performed with eight energy degraders will allow to uniquely identify each beam energy, from two or more measurement points on the slope of each electron energy measurement as described in relation to FIG. 7.

FIG. 7 is representing a particular example of a set of electron PDDs (Percent Depth Dose) corresponding to energies of 4, 6, 8, 9, 10, 12, 15, 18, 20, 22 MeV, with corresponding set of 8 values of water-equivalent depths corresponding to a set of 8 degraders.

Figure 8:
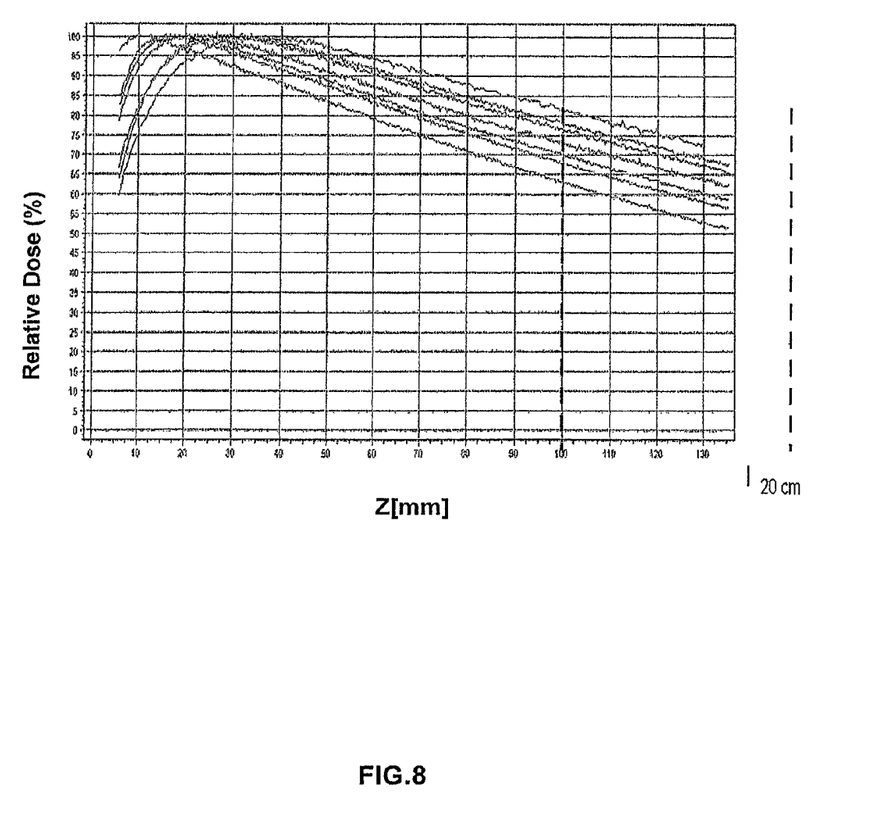
FIG. 8 represents the relative dose measured in function of the depth in water for various photon beam energies and is an example of a measurement of the photon energy performed by means of two ionisation chamber radiation detectors beneath the corresponding two energy degraders present on the photon build-up plate of the device as described in FIG. 1.

In a an similar way, the results of the energy measurement performed with the photon energy degraders will allow to uniquely identify each beam energy, from two or more measurement points on the slope of each photon energy measurement as described in FIG. 8.

FIG. 8 represents the relative dose in % measured in function of the depth in water (Z [mm]) for various photon beam energies. It represents a particular example of a set of photon PDDs corresponding to energies of 4, 6, 8, 9, 10, 12, 15, 18, 20, 25 MeV, with corresponding 2 values of water-equivalent depths corresponding to a set of 2 degraders (100 mm and 150 mm, represented by two vertical dashed lines).

The above description should be considered as illustrative examples not limiting the scope of the invention. For example, the method for verifying the positions of a leaf of a MLC should also be considered as covering a MLC comprising a single leaf on each side, i.e. jaws.

The invention claimed is:

1. A method for verifying quantities of interest of a radiation beam in a radiation therapy apparatus comprising a multi-leaf collimator provided with leaves, comprising the steps of:
    providing a dosimetry device comprising an active area which includes individual detectors;
    the active area comprising a limited number of lines of radiation detectors and a number of extra radiation detectors dedicated to energy measurements of electrons or photons;
    the dosimetry device further comprising a build-up plate with a plurality of energy degraders, the energy degraders being located upstream from the extra radiation detectors in the path of the radiation beam;

adapting the dosimetry device for determining positions of leaves of a multi-leaf collimator in an Intensity Modulated Radiation Therapy apparatus, wherein the limited number of lines of radiation detectors comprises at least one extra line of radiation detectors dedicated to measurement and determination of projection of the leaves position at isocenter of the Intensity Modulated Radiation Therapy apparatus, the at least one extra line of radiation detectors being located at about expected positions of the projection of the leaves;

positioning the leaves of the multi-leaf collimator in a predetermined position;

delivering a radiation dose to the dosimetry device through the multi-leaf collimator;

measuring dose absorbed by a plurality of radiation detectors of a line of radiation detectors located in a penumbra region of one of the leaves; and determining the quantities of interest by fitting measured doses with a function, wherein the quantities of interest comprise:

a position of one of the leaves;

a position and width of the penumbra region;

positions where a beam profile reaches a given percent of a value of the beam in the center of the beam;

skewness of the beam;

flatness of the beam; and position of the center of the radiation beam.

2. A method for verifying quantities of interest of a radiation beam in a radiation therapy apparatus with an multi-leaf collimator provided with jaws, comprising the steps of:

providing a dosimetry device comprising an active area which includes individual detectors;

the active area comprising a limited number of lines of radiation detectors and a number of extra radiation detectors dedicated to energy measurements of electrons or photons;

the dosimetry device further comprising a build-up plate with a plurality of energy degraders, the energy degraders being located upstream from the extra radiation detectors in the path of the radiation beam;

positioning the leaves in a predetermined position;

delivering a radiation dose to the dosimetry device through the multi-leaf collimator;

measuring dose absorbed by a plurality of radiation detectors of a line of radiation detectors located in a penumbra region of one of the leaves;

and determining the quantities of interest by fitting measured doses with a function, wherein the quantities of interest comprise:

a position of one of the jaws;

a position and width of the penumbra region;

positions where a beam profile reaches a given percent of a value of the beam in the center of the beam;

skewness of the beam;

flatness of the beam; and position of the center of the radiation beam.

3. A method for verifying quantities of interest of a radiation beam in a radiation therapy apparatus comprising a multi-leaf collimator provided with leaves, comprising the steps of:

providing the dosimetry device comprising one or more lines of radiation detectors;

positioning the leaves of the multi-leaf collimator in a predetermined position;

delivering a radiation dose to the dosimetry device through the multi-leaf collimator;

measuring dose absorbed by a plurality of radiation detectors of a line of radiation detectors located in a penumbra region of one of the leaves; and determining the quantities of interest by fitting measured doses with a function, wherein the quantities of interest comprise a position of one of the leaves, a position and width of the penumbra region, positions where a beam profile reaches a given percent of a value of the beam in the center of the beam, skewness of the beam, flatness of the beam, and position of the center of the radiation beam.

4. A method for verifying quantities of interest of a radiation beam in a radiation therapy apparatus with an multi-leaf collimator provided with jaws, comprising the steps of:

providing a dosimetry device comprising one or more lines of radiation detectors;

positioning the jaws in a predetermined position;

delivering a radiation dose to the dosimetry device through the multi-leaf collimator;

measuring the dose absorbed by a plurality of radiation detectors of a line of radiation detectors located in a penumbra region of the jaw; and determining the quantities of interest by fitting measured doses with a function, wherein the quantities of interest comprise a position of one of the jaws, a position and width of the penumbra region, positions where a beam profile reaches a given percent of a value of the beam in the center of the beam, skewness of the beam, flatness of the beam, and position of the center of the radiation beam.

* * * * *